United States Patent
Hunter et al.

[11] Patent Number: 6,154,669
[45] Date of Patent: Nov. 28, 2000

[54] HEADSET FOR EEG MEASUREMENTS

[75] Inventors: David B. Hunter, King of Prussia; Kenneth B. McCarraher, Pottstown, both of Pa.; Kenneth P. Fratto, Holmdel, N.J.; Richard M. Brueggman, Bethel Park, Pa.; Tomas J. Stenstrom, Ft. Washington, Pa.; Harlan I. Gustafson, Jr., Limerick, Pa.

[73] Assignee: Capita Systems, Inc., King of Prussia, Pa.

[21] Appl. No.: 09/187,525

[22] Filed: Nov. 6, 1998

[51] Int. Cl.$^7$ .................................................. A61B 5/0478
[52] U.S. Cl. ........................... 600/383; 600/393; 600/395; 607/139
[58] Field of Search .................... 600/372, 383, 600/384, 391, 392, 393, 395, 396; 607/145, 152, 139

[56] References Cited

U.S. PATENT DOCUMENTS

| | | |
|---|---|---|
| 1,679,245 | 7/1928 | Gaertner ................................... 607/139 |
| 3,659,614 | 5/1972 | Jankelson ................................. 607/139 |
| 4,088,133 | 5/1978 | Twentier .................................... 606/32 |
| 4,109,648 | 8/1978 | Larke et al. . |
| 4,122,843 | 10/1978 | Zdrojkowski ........................... 600/382 |
| 4,454,007 | 6/1984 | Pace . |
| 4,583,549 | 4/1986 | Manoli .................................... 600/393 |
| 4,638,807 | 1/1987 | Ryder . |
| 4,669,479 | 6/1987 | Dunseath, Jr. ........................... 600/393 |
| 4,685,467 | 8/1987 | Cartmell et al. . |
| 4,928,696 | 5/1990 | Henderson et al. . |
| 4,967,038 | 10/1990 | Gevins et al. . |
| 5,273,037 | 12/1993 | Itil et al. . |
| 5,348,006 | 9/1994 | Tucker . |
| 5,357,957 | 10/1994 | Itil et al. . |
| 5,449,002 | 9/1995 | Goldman . |
| 5,479,934 | 1/1996 | Imran . |
| 5,608,599 | 3/1997 | Goldman . |
| 5,662,123 | 9/1997 | Goldman . |

FOREIGN PATENT DOCUMENTS

| | | | |
|---|---|---|---|
| 0000759 | 2/1979 | European Pat. Off. ............... | 607/149 |
| 2735050 | 2/1979 | Germany ............................... | 600/395 |

*Primary Examiner*—Lee Cohen
*Attorney, Agent, or Firm*—Oblon, Spivak, McClelland, Maier & Neustadt, P.C.

[57] ABSTRACT

A headset and system for taking EEG measurements on the head of a test subject. The headset has a plurality of electrode sensors in predetermined anatomical positions on the head of a subject to take EEG measurements, for example of the subject's response to certain stimuli. The electrode sensors are formed of dry conductive foam rubber pads attached to conductor elements. An individual shielded cable is attached to each sensor to carry the detected signal to a signal processor. The sensors may be formed of a carbon impregnated foam rubber pad that offers high conductivity. The sensors do not require wetting agent, and thus can be used in a very time efficient manner, and can be easily replaced for sanitary considerations.

10 Claims, 2 Drawing Sheets

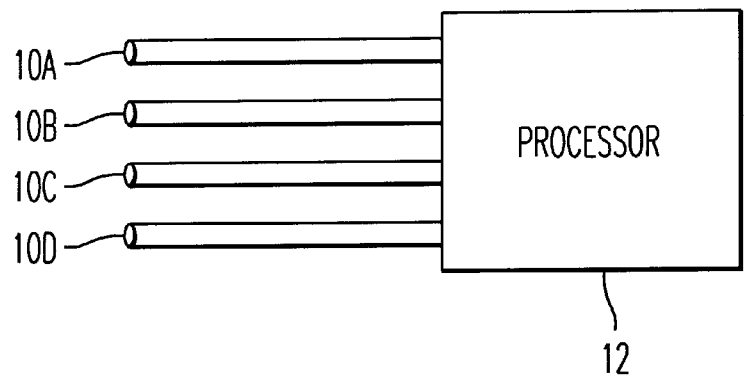
*FIG. 2*
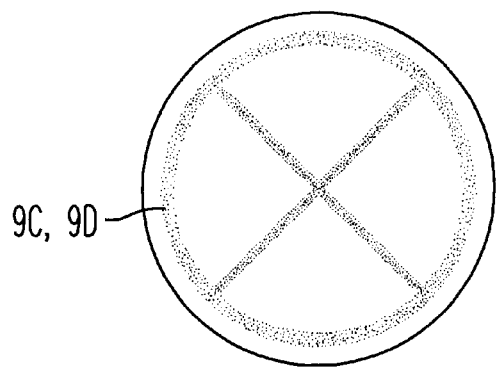    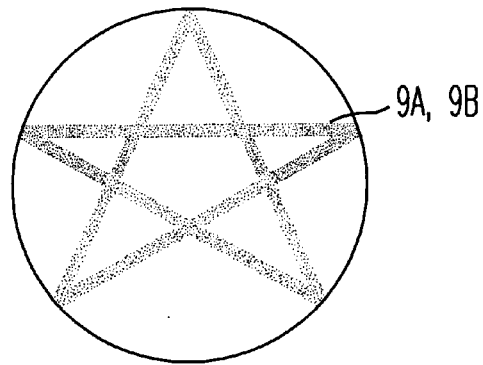
*FIG. 3A*    *FIG. 3B*

HEADSET FOR EEG MEASUREMENTS

BACKGROUND OF THE INVENTION

1. Field of the Invention

The present invention is directed to a headset for making EEG (electroencephalogram) measurements of a subject.

2. Discussion of the Background

It is often desirable to take EEG measurements of a subject to determine the brain activity of the subject. There are many medical applications that require testing and measuring of EEG signals to determine a subject's medical condition. There are also instances in which it is desirable to test or measure a subject's brain activity for other purposes.

One such other purpose is to test a subject's brain activity to measure the subject's interest to certain stimuli. For example, it is desirable to be able to test a subject's attention level to a particular marketing idea, television advertisement, or other promotional tool. Such testing is currently performed by attaching sensors to a subject through a foam sponge wetted with a saline solution to be conductive. These sensors can be attached to a headset.

One problem associated with testing a number of subjects using a headset with such wetted sensors is the problem of maintaining sanitary conditions for the test subjects, and also being able to maintain sanitary conditions in a time efficient manner. This problem is particularly important when the sensor is used in commercial contexts since it may be important to test as many subjects as possible. Another problem associated with testing a number of subjects is that it is expensive to use a headset for one individual and then discard it for sanitary considerations. Many of these problems arise from utilizing a wetting agent for the sensors to be conductive and detect brain activity. In these ways, the use of a wetting agent is time consuming and unsanitary if the headset is used by more than one subject.

SUMMARY OF THE INVENTION

Accordingly, the applicants of the present invention have recognized that there is a need for a novel headset electrode sensor apparatus which can generate a signal to measure brain activity, and yet which is still simple, easy to manufacture, inexpensive, and time efficient to use.

The applicants of the present invention have specifically recognized that there is a need for a novel headset electrode sensor apparatus which does not require a wetting agent, but yet which is still sufficiently conductive to produce an accurate signal. There is further a need for a novel headset electrode sensor assembly which is inexpensive and sanitary by virtue of the fact that the sensors are maintained dry and can be easily replaced if necessary, and yet which are still highly conductive.

Accordingly, it is an object of the present invention to provide a novel headset electrode sensor assembly which provides a good signal of brain activity and yet which is inexpensive, sanitary, and time efficient to use, and which further does not require the use of a wetting agent.

It is a further object of the present invention to provide a novel headset electrode sensor assembly which still provides efficient operation and which has easily replaceable electrode sensors.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein:

FIG. 2 shows a structure of outputting signals from the electrode sensors; and

FIGS. 3(A) and 3(B) show a specific formation which the electrode sensors can take in the present invention.

DESCRIPTION OF THE PREFERRED EMBODIMENTS

Figure 1A:
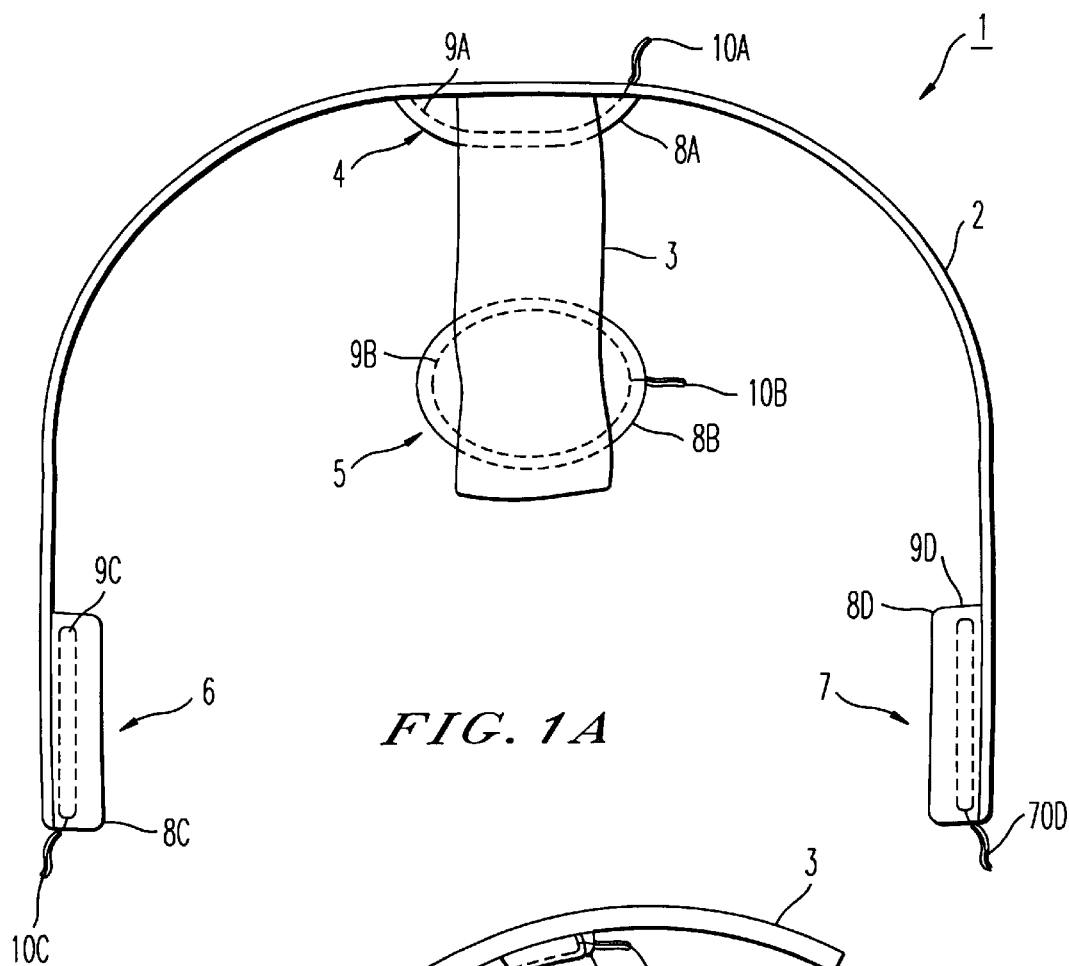
FIGS. 1(A) and 1(B) show an embodiment of the present invention of a headset assembly with electrode sensors.
Figure 1B:
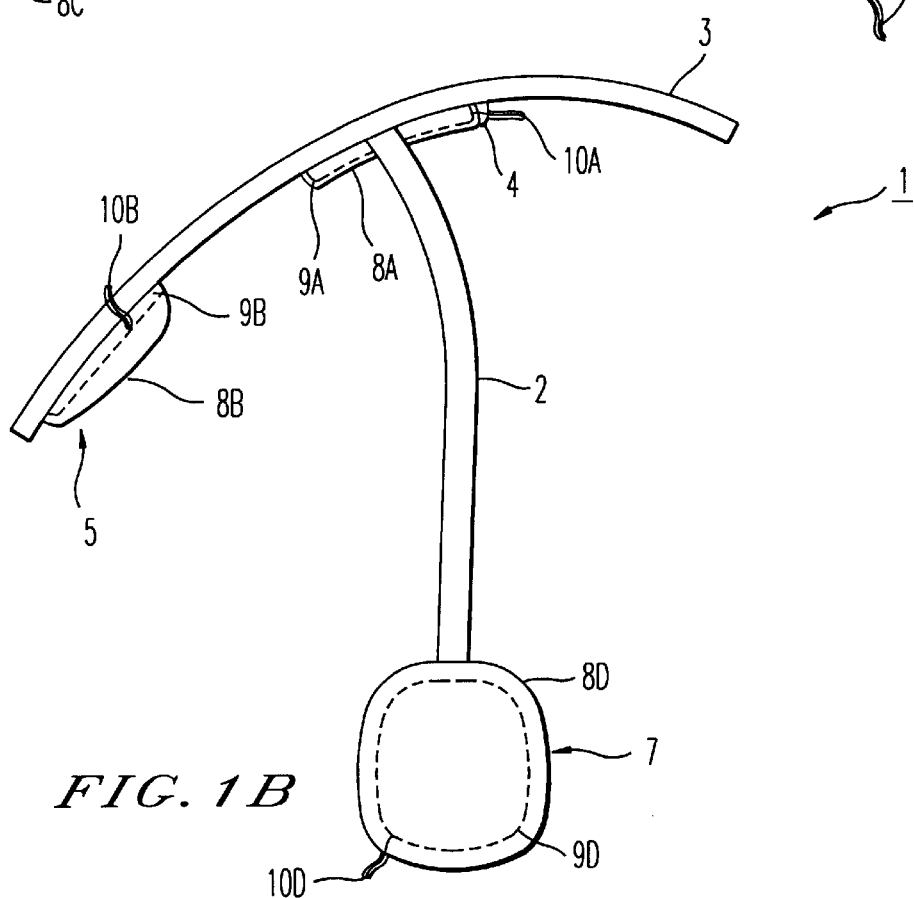

Referring now to the drawings, wherein like reference numerals designate identical or corresponding parts throughout the several views, and more particularly to FIGS. 1(A) and 1(B) thereof, a headset electrode sensor apparatus of the present invention is shown in which FIG. 1(A) is a front view and FIG. 1(B) is a side view.

As shown in FIGS. 1(A) and 1(B), the present invention is directed to a headset 1 which includes a headset base 2. The headset base 2 can be a generic stereo headphone without the speakers formed at the plastic casing at the earphone locations, and as such the headset base 2 is inexpensive and easy to manufacture. As in a stereo headphone the length of the headset base 2 can be adjusted. The headset base 2 is a member which extends from one ear area of a subject, over a top of the subject's head, to the other ear area of the subject, again as in a generic stereo headphone. The headset 1 includes a further member 3 attached as a crossbar to a middle of the headset base 2 and extending perpendicular to the headset base 2. This crossbar member 3 extends, when the headset 1 is placed on a subject's head, from approximately a center of the subject's forehead to a back top of the subject's head. These two members 2 and 3 are connected at their point of intersection at the top middle of a subject's head when the headset 1 is placed on the subject's head. The headset structure thus rests comfortably on a subject's head when in use.

The headset 1 further includes four electrode sensors 4–7 which can be removably attached to the headset 1 at varying positions. These electrode sensors 4–7 can be secured to the headset 1 by VELCRO, snaps, or any other suitable attachments which allow easy placement, removal, and replacement of the sensors 4–7.

The sensor 4 is removably secured to the headset 1 at the point of intersection of the crossbar member 3 and headset base 2. The sensor 4 includes a conductive carbon foam pad 8A, a conductive member 9A in contact with the carbon foam pad 8A, and a shielded cable wire 10A attached to the conductive member 9A. Such a shielded cable wire 10A can be permanently secured to the conductive member 9A, for example by soldering, or can be detachably secured to the conductive member 9A, for example by a jack and plug connection, and of course other attachment methods can be utilized.

A further sensor 5 is attached to the crossbar 3 at a position corresponding to an approximate center of a subject's forehead when the subject is wearing the headset 1. The sensor 5 includes a carbon foam pad 8B, a conductive member 9B, and a shielded cable wire 10B secured to the conductive member 9B by any of the above-noted attachments.

Respective sensors 6 and 7 are attached to the headset base 2 at positions corresponding to ear lobe areas of the subject. These sensors 6 and 7 are attached at positions where the speakers in stereo headphones are provided. Further, these sensors 6, 7 also include respective carbon foam pads 8C, 8D, conductive members 9C, 9D, and respective shielded cable wires 10C and 10D attached to the respective conductive members 9C, 9D by any of the attachment methods noted above.

The shielded cables wires 10A–10D can be secured to the headset base 2 or crossbar member 3 and can then be bundled together. As shown in FIG. 2, such bundled shielded cable wires 10A–10D can provide their outputs to a processor 12, e.g. a computer system, where independent signals can be processed related to measurement of a subject's brain wave activity. These shielded cable wires 10A–10B are preferably shielded to minimize any interference between the signals transmitted on these cables, although this may not be necessary in certain instances.

As noted above, each of the sensors 4–7 is formed of a respective outer carbon foam pad 8A–8D which contacts a subject and an inner conductive member 9A–9B. The inner conductive members 9A–9B can typically be made of a copper braid element.

Each sensor 4–7 is formed as follows. A plastic casing is provided in the headset 1 and the respective conductive copper braid element 9A–9D is laid in the plastic casing, heat-bonded, and then pressed into place at a desired pattern. The respective shielded cable wires 10A–10D are then soldered to the conductive copper braid elements 9A–9D and are fed out of a back or a side of the plastic casing. If a jack and plug attachment is desired, then the jack is attached to the conductive copper braid elements 9A–9D. The carbon foam pads 8A–8D, which are preferably of an anti-static grade, are then glued on top of the conductive copper braid elements 9A–9D to contact the conductive copper braid elements 9A–9D and are pressed into place. A fast bonding glue can be used to attach the carbon foam pads 8A–8D to the plastic casing. It is preferable if the glue is not applied directly to the conductive copper braid elements 9A–9D.

The carbon foam pads 8A–8D may preferably be formed of 3M VELOSTAT 2882 series "Cross-linked Polyethylene electrically conductive foam". The carbon can be compounded directly into polyethylene and the carbon foam pads 8A–8D are estimated to have a 25% carbon composition, and in testing two probes placed in such carbon foam pads 8A–8D one inch apart will measure no more than 1000 ohms resistance.

The conductive copper braid elements 9A–9D may have specific structures such as shown in FIGS. 3(A) and 3(B). FIG. 3(A) shows the shape of the conductive copper braid elements 9C, 9D of respective sensors 6 and 7 located in the ear lobe positions of the headset 1. These conductive copper braid elements 9C, 9D may be configured as shown in FIG. 3(A) to add stability to the backing of the carbon foam pads 8A, 8B. This may be necessary if generic stereo headphones are used for the headset base 2 and a plastic casing for the earphones is hollowed out. In this instance, the conductive copper braid elements 9C, 9D are laid into the circumference of the inner plastic casing and two pieces of the conductive copper braid elements 9C, 9D are then soldered to the circle in an "X" pattern. This structure provides a stiffer backing for the carbon foam pads 8C, 8D. The solder used in this instance can be electronic solder with a 60-40 composition of lead and tin.

The conductive copper braid elements 9A, 9B formed in the sensors 4 and 5 may have a structure such as shown in FIG. 3(B) of a "star" shape. This shape maximizes a surface area of conductive copper braid elements 9A, 9B in contact with the carbon foam pads 8A, 8B. Further, the "star" pattern allows a continuous piece of copper braid conductor to be used, folded at each vertex.

With the structure noted above, the headset 1 provides the easy placement of four sensors at appropriate positions on a subject for measuring brain waves. The brain wave activities are picked up through the carbon foam pads 8A–8D, which are conductive, supplied to the conductive copper braid elements 9A–9D in contact with the carbon foam pads, and brain wave signals are then transmitted by the shielded cable wires 10A–10D to signal processor 12. With this structure in the present invention, brain wave signals can be detected without utilizing a wetting agent as the conductive carbon foam pads 8A–8D act as a conductor of the brain waves. By not requiring a wetting agent, sanitary conditions are significantly improved. Further, such a device can be used in an extremely time efficient manner by not requiring any preparation of a subject, again particularly with respect to not requiring a wetting agent. Also, such a headset 1 in the present invention is inexpensive and simple to manufacture, and the sensor units can be easily replaced.

Obviously, numerous additional benefits of the present invention are achieved by the structure of the present invention. Moreover, numerous additional modifications and variations of the present invention are possible in light of the above teachings. It is therefore to be understood that within the scope of the appended claims, the present invention may be practiced otherwise than as specifically described herein.

What is claimed is:

1. A headset for measuring brain waves, comprising:

a headset base extending in a first direction and including at least a first dry conductive foam configured to contact a subject at an ear lobe area of the subject when the subject is wearing said headset;

a crossbar member attached to said base and extending in a second direction different than the first direction and including at least a second dry conductive foam pad configured to contact the subject when the subject is wearing the headset;

at least first and second conductors respectively in contact with said first and second dry conductive foam pads; and a third conductive foam pad disposed at a position where said headset base and said crossbar member cross each other, and a third conductor in contact with said third conductive foam pad.

2. A system for measuring brain waves, comprising:

a headset including:

a headset base extending in a first direction and including at least a first dry conductive foam pad configured to contact a subject at an ear lobe area of the subject when the subject is wearing said headset;

a crossbar member attached to said headset base and extending in a second direction different than the first direction and including at least a second dry conductive foam pad configured to contact the subject when the subject is wearing said headset;

at least first and second conductors respectively in contact with said at least first and second dry conductive foam pads; and a processor receiving signals from the at least first and second conductors.

3. A system according to claim 2, wherein the at least first and second dry conductive foam pads each include a foam pad impregnated with carbon.

4. A system according to claim 3, wherein the at least first and second conductors each include a copper braid.

5. A system according to claim 4, further comprising a shielded cable wire connected to the at least first and second conductors to supply the signals for the processor.

6. A system according to claim 3, further comprising a shielded cable wire connected to the at least first and second conductors to supply the signals to the processor.

7. A system according to claim 2, wherein the at least first and second conductors each include a copper braid.

8. A system according to claim 7, further comprising a shielded cable wire connected to the at least first and second conductors to supply the signals to the processor.

9. A system according to claim 2, further comprising a shielded cable wire connected to the at least first and second conductors to supply the signals to the processor.

10. A system according to claim 2, further comprising a third conductive foam pad disposed at a position where said headset base and said crossbar member cross each other, and a third conductor in contact with said third conductive foam pad.

* * * * *